(12) United States Patent
Watanabe

(10) Patent No.: US 7,298,824 B2
(45) Date of Patent: Nov. 20, 2007

(54) X-RAY DIAGNOSTIC APPARATUS

(75) Inventor: Izumi Watanabe, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/277,003

(22) Filed: Mar. 20, 2006

(65) Prior Publication Data
US 2006/0215817 A1    Sep. 28, 2006

(30) Foreign Application Priority Data
Mar. 22, 2005    (JP)    ............... 2005-081989

(51) Int. Cl.
*H05G 1/30*    (2006.01)
(52) U.S. Cl. .................... 378/114; 378/197
(58) Field of Classification Search ............... 378/102, 378/114, 115, 117, 195–198, 208–209
See application file for complete search history.

(56) References Cited
U.S. PATENT DOCUMENTS
6,236,712 B1 *   5/2001   Tomasetti et al. ......... 378/114
6,474,865 B2 *   11/2002   Nakajo ....................... 378/209

FOREIGN PATENT DOCUMENTS
JP    2001-137222    5/2001

\* cited by examiner

*Primary Examiner*—Hoon Song
(74) *Attorney, Agent, or Firm*—Oblon, Spivak, McClelland, Maier & Neustadt, P.C.

(57) ABSTRACT

An X-ray diagnostic apparatus includes an X-ray generating unit which generates X-rays, an X-ray detecting unit which detects X-rays transmitted through a subject, a C-arm on which the X-ray generating unit and the X-ray detecting unit are mounted, a support mechanism which movably supports the C-arm, a high voltage generating unit which generates a high voltage for generating X-rays from the X-ray generating unit, a first foot switch to input a first user instruction associated with generation of the X-rays, a second foot switch to input a second user instruction associated with movement of the C-arm, and a control unit which controls the high voltage generating unit in accordance with the input of the first user instruction and controls the support mechanism in accordance with the input of the second user instruction.

14 Claims, 8 Drawing Sheets

Preset Parameters

Fluoroscopy/automatic positioning

○ Only automatic positioning is executed
◉ Fluoroscopy/automatic positioning are executed
○ Fluoroscopy is always performed while SW is ON
◉ Fluoroscopy is performed upon completion of automatic positioning
○ Fluoroscopy is started before completion of automatic positioning

Reference image display/automatic positioning

☑ Automatic display of reference image is performed
◉ Switching to registered image is performed
○ Automatic search is made from acquired images

Holding device registration information

☑ C-arm rotational angle/ C-arm slide angle
☐ SID
☐ Detector rotational angle
☐ Column angle
☐ Column longitudinal position/ widthwise position
☐ X-ray stop aperture position
☐ Filter position
☐ Bed position information
☐ Top height
☐ Top longitudinal position
☐ Top widthwise position
☐ Top rotational angle

Automatic positioning unit

☑ C-arm rotational angle/ C-arm slide angle
☐ SID
☐ Detector rotational angle
☐ Column angle
☐ Column longitudinal position/ widthwise position
☐ X-ray stop aperture position
☐ Filter position
☐ Bed position information
☐ Top height
☐ Top longitudinal position
☐ Top widthwise position
☐ Top rotational angle

F I G. 5

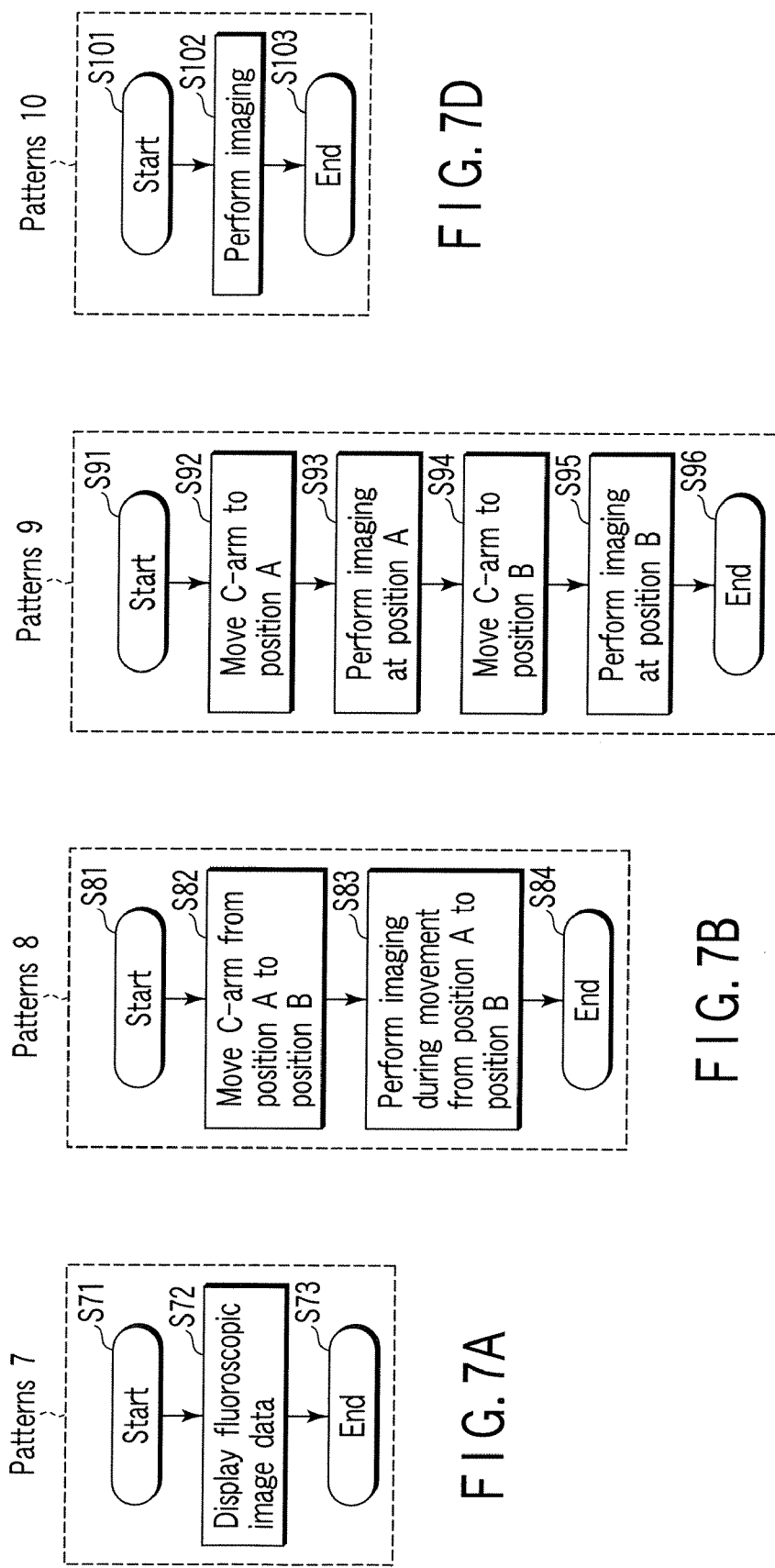

X-RAY DIAGNOSTIC APPARATUS

CROSS-REFERENCE TO RELATED APPLICATIONS

This application is based upon and claims the benefit of priority from prior Japanese Patent Application No. 2005-081989, filed Mar. 22, 2005, the entire contents of which are incorporated herein by reference.

BACKGROUND OF THE INVENTION

1. Field of the Invention

The present invention relates to an X-ray diagnostic apparatus having a C-arm.

2. Description of the Related Art

In diagnosis or medical treatment based on angiography, a device such as a guide wire or catheter is inserted into a blood vessel. An operator advances a device to a morbid region of a subject in diagnosis of the morbid region while referring to fluoroscopic image data obtained by fluoroscopy and reference image data obtained by imaging at the same position as that of the fluoroscopic image data upon injecting a contrast medium in advance by using an X-ray diagnostic apparatus for circulatory organs.

In addition, in many cases, an operator advances a device to a morbid region while calling up and checking, on a monitor, fluoroscopic image data for displaying a blood vessel structure in real time by temporarily injecting a small amount of contrast medium into the blood vessel and reference image data.

Furthermore, an operator often advances a device to a morbid region while displaying and checking, on a monitor, image data (fluoroscopic road map image data) in which a blood vessel image and a guide wire image are extracted by subtraction processing for fluoroscopic image data for displaying a blood vessel structure, which is obtained in real time, and reference image data obtained in advance by imaging at the same position as that of the fluoroscopic image data.

When a morbid region to be treated is determined to some extent, an operator advances a device inserted into the blood vessel or performs medical treatment while observing the morbid region from at least two positions by displaying fluoroscopic image data and reference image data or fluoroscopic road map image data concerning the morbid region on the monitor. In addition, an observation region is imaged as needed.

An X-ray diagnostic apparatus for circulatory organs comprises an X-ray generating unit which applies X-rays to a subject, an X-ray detecting unit which is positioned to face the X-ray generating unit through the subject and detects X-rays, and a C-arm which holds the X-ray generating unit and the X-ray detecting unit. It is known that X-ray diagnostic apparatuses for circulatory organs include a single plane system comprising one C-arm and a biplane system comprising two C-arms (see, for example, Jpn. Pat. Appln. KOKAI Publication No. 2001-137222).

In the present circumstances, although an X-ray diagnostic apparatus of the biplane system requires no complicated operation for the movement of the C-arms because observations from two positions can be simultaneously performed by using the two C-arms, the apparatus demands a large installation area and is expensive, and hence its installation is limited.

In contrast, an X-ray diagnostic apparatus of the single plane system does not demand a large installation area and is inexpensive as compared with that of the biplane system, and hence is installed in many places.

In the single plane system, however, every time the observation position is changed, the C-arm must be moved, and image data such as fluoroscopic image data, reference image data, and fluoroscopic road map image data at the position to which the C-arm is moved must be displayed. These operations must be manually performed using an operating unit. Such operations are cumbersome and difficult for an operator who manually operates a device such as a catheter or guide wire during diagnosis or medical treatment.

BRIEF SUMMARY OF THE INVENTION

It is an object of the present invention to improve operability in moving a C-arm and performing imaging operation in an X-ray diagnostic apparatus.

According to a first aspect of the present invention, there is provided an X-ray diagnostic apparatus comprising an X-ray generating unit which generates X-rays, an X-ray detecting unit which detects X-rays transmitted through a subject, a C-arm on which the X-ray generating unit and the X-ray detecting unit are mounted, a support mechanism which movably supports the C-arm, a high voltage generating unit which generates a high voltage for generating X-rays from the X-ray generating unit, a first foot switch to input a first user instruction associated with generation of the X-rays, a second foot switch to input a second user instruction associated with movement of the C-arm, and a control unit which controls the high voltage generating unit in accordance with the input of the first user instruction and controls the support mechanism in accordance with the input of the second user instruction.

According to a second aspect of the present invention, there is provided an X-ray diagnostic apparatus comprising an X-ray generating unit which generates X-rays, an X-ray detecting unit which detects X-rays transmitted through a subject, a C-arm on which the X-ray generating unit and the X-ray detecting unit are mounted, a support mechanism which movably supports the C-arm, a high voltage generating unit which generates a high voltage for generating X-rays from the X-ray generating unit, a plurality of foot switches to input a plurality of kinds of user instructions, and a control unit which controls at least one of the high voltage generating unit and the support mechanism in accordance with the input of one of the plurality of kinds of user instructions.

According to a third aspect of the present invention, there is provided an X-ray diagnostic apparatus comprising an X-ray generating unit which generates X-rays, an X-ray detecting unit which detects X-rays transmitted through a subject, a C-arm on which the X-ray generating unit and the X-ray detecting unit are mounted, a support mechanism which movably supports the C-arm, a high voltage generating unit which generates a high voltage for generating X-rays from the X-ray generating unit, a foot switch to input a user instruction, a preset window generating unit which generates a preset window for presetting an action associated with at least one of generation of the X-rays and movement of the C-arm in accordance with the input of the user instruction, and a control unit which controls at least one of the high voltage generating unit and the support mechanism in accordance with the preset action when the user instruction is input.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the present invention.

FIG. 5 is a view showing an operation condition setting window according to this embodiment;

FIG. 7A is a flowchart showing a sequence for operation pattern 7 according to this embodiment;

FIG. 7B is a flowchart showing a sequence for operation pattern 8 according to this embodiment;

FIG. 7C is a flowchart showing a sequence for operation pattern 9 according to this embodiment;

FIG. 7D is a flowchart showing a sequence for operation pattern 10 according to this embodiment.

DETAILED DESCRIPTION OF THE INVENTION

Figure 1:
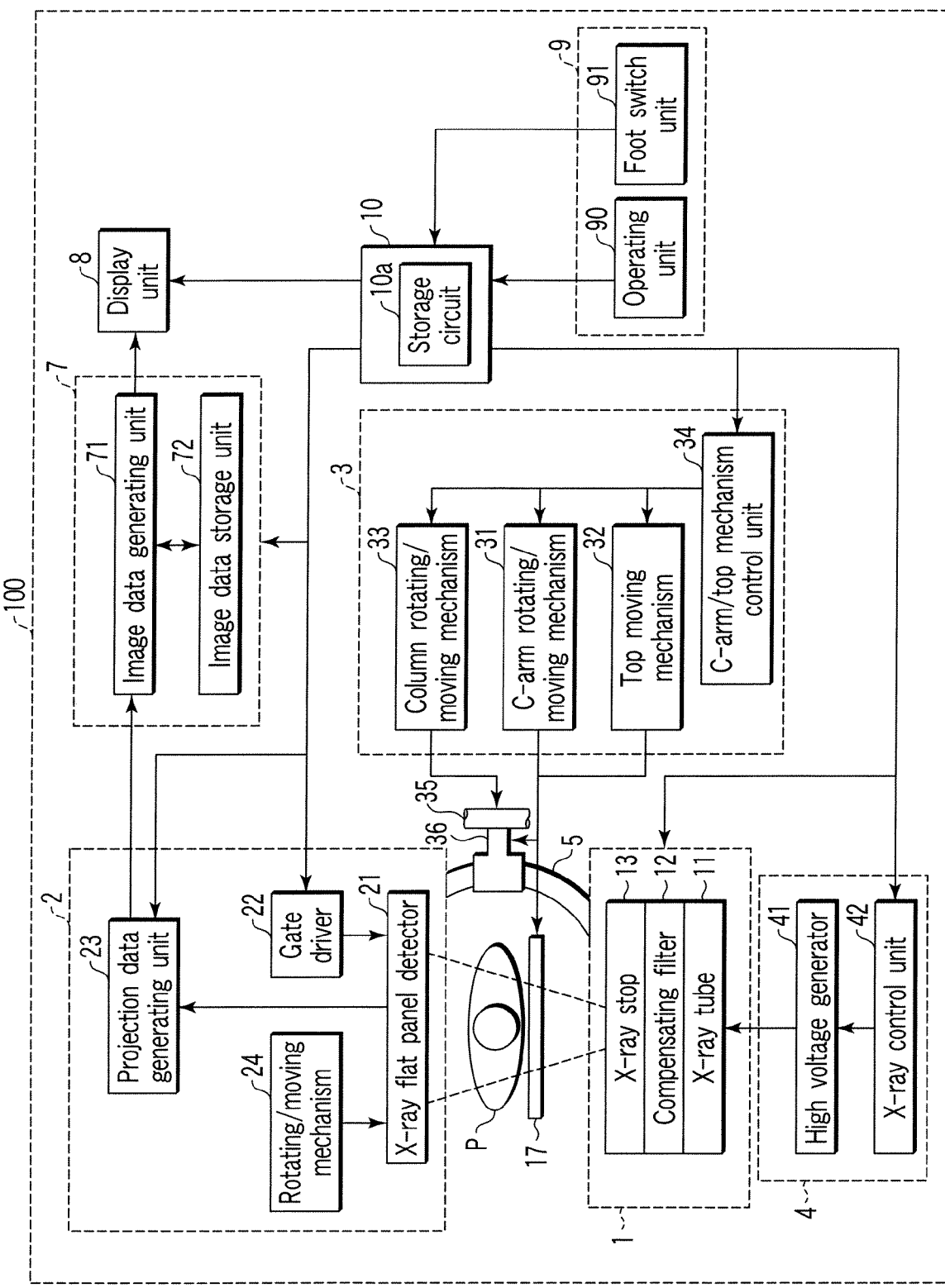
FIG. 1 is a block diagram showing the arrangement of an X-ray diagnostic apparatus according to an embodiment of the present invention.

An X-ray diagnostic apparatus according to an embodiment of the present invention will be described with reference to the views of the accompanying drawing. FIG. 1 is a block diagram showing the arrangement of an X-ray diagnostic apparatus according to this embodiment. An X-ray diagnostic apparatus 100 comprises an X-ray generating unit 1 which generates X-rays, an X-ray detecting unit 2 which detects X-rays transmitted through a subject P, a C-arm 5 on which an X-ray generating unit 1 and an X-ray detecting unit 2 are mounted, a top 17 on which the subject P is placed, and a high voltage control unit 4 which generates a high voltage for generating X-rays from the X-ray generating unit 1.

The X-ray diagnostic apparatus 100 comprises a mechanical unit 3 which moves the C-arm 5, the top 17, and the like, an image data processing unit 7 which generates and stores various kinds of image data from X-ray projection data generated by the X-ray detecting unit 2, and a display unit 8 which displays image data output from the image data processing unit 7.

The X-ray diagnostic apparatus 100 comprises an operating unit 9 for inputting subject information, e.g., the ID and name of the subject P, photographing conditions, display conditions, and user instructions associated with the generation of X-rays and the movement of the C-arm 5 (to be described later), and a system control unit 10 which systematically controls the respective units of the X-ray diagnostic apparatus 100.

The X-ray generating unit 1 comprises an X-ray tube 11 which applies X-rays to the subject P, a compensating filter 12 which reduces X-ray absorption differences, and an X-ray stop 13 which sets the application range of X-rays applied from the X-ray tube 11.

A compensating filter 12 is placed between the X-ray tube 11 and the subject P and comprises a filter and a filter driving mechanism which moves the filter. When this filter driving mechanism sets the filter at a position as a photographing condition, some of X-rays transmitted through the filter are absorbed.

The X-ray stop 13 is placed between the X-ray tube 11 and the subject P and comprises upper and lower blades and an X-ray stop aperture driving mechanism which moves the upper and lower blades. When this X-ray stop aperture driving mechanism sets the upper and lower blades at positions as photographing conditions, an X-ray application range is set.

The X-ray detecting unit 2 comprises an X-ray flat panel detector 21 which detects X-rays transmitted through the subject P, converts the X-rays into electric charges, and stores them, a gate driver 22 which reads out electric charges stored in the X-ray flat panel detector 21, a projection data generating unit 23 which generates X-ray projection data from the read electric charge, and a rotating/moving mechanism 24 which moves the X-ray flat panel detector 21. Note that the detection of X-rays by X-ray detecting unit 2 may be performed by using an image intensifier which converts X-rays into light and then converts the light into electric charges.

The flat panel detector 21 is placed to face the X-ray generating unit 1 through the subject P and is formed by two-dimensionally arraying minute detection elements in the column and line directions. Each detection element comprises a photoelectric film which detects X-rays and generates electric charges in accordance with the amount of incident X-rays, an electric charge storage capacitor which stores electric charges generated in the photoelectric film, and a TFT (Thin-Film Transistor) which reads out electric charges stored in the electric charge storage capacitor at a predetermined timing.

The projection data generating unit 23 parallelly reads out electric charges from the flat panel detector 21 on a line basis, and digitally converts them into a digital signal to generate X-ray projection data.

The rotating/moving mechanism 24 rotates the X-ray flat panel detector 21 about an axis perpendicular to its X-ray detection surface as a rotation axis and moves the X-ray flat panel detector 21 back and forth in the direction of the X-ray tube 11. With the back-and-forth movement of the X-ray flat panel detector 21, a distance (SID) between the stop 15 and the X-ray flat panel detector 21 is set as a photographing condition.

The mechanical unit 3 comprises a C-arm rotating/moving mechanism 31 which rotates and slides the C-arm 5 on which the X-ray generating unit 1 and the X-ray detecting unit 2 are mounted, a top moving mechanism 32 which moves the top 17 in the longitudinal direction, widthwise direction, and vertical direction, and rotates the top 17 in a horizontal state, a column rotating/moving mechanism 33 which rotates and moves a column 35 which holds the C-arm 5, and a C-arm/top mechanism control unit 34 which controls the C-arm rotating/moving mechanism 31, top moving mechanism 32, and column rotating/moving mechanism 33.

Figure 2B:
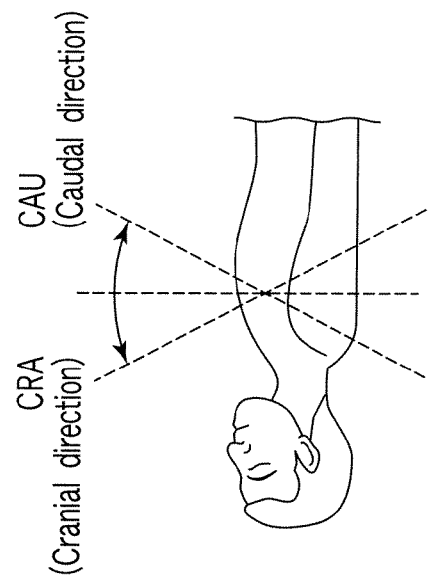
FIG. 2B is a view showing a subject in an oblique direction in the X-ray diagnostic apparatus in FIG. 1.
Figure 2C:
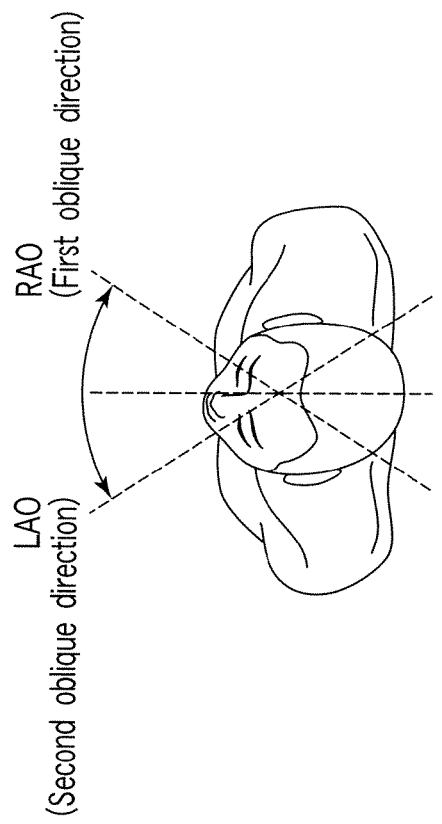
FIG. 2C is a view showing the subject in the cranial/caudal direction in the X-ray diagnostic apparatus in FIG. 1.
Figure 2A:
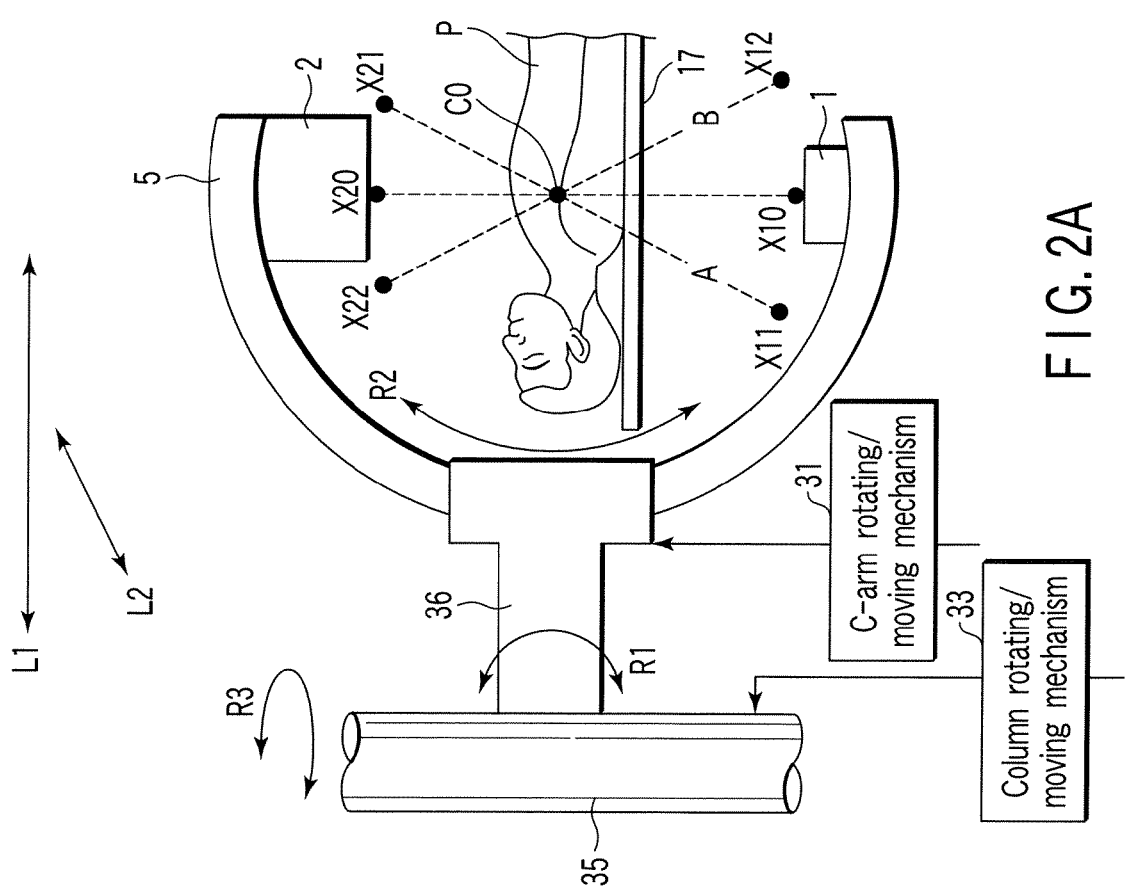
FIG. 2A is a side view of a C-arm and the like in FIG. 1.

FIGS. 2A, 2B, and 2C are views for explaining the moving directions of the X-ray generating unit 1 and the X-ray detecting unit 2 which are driven by the C-arm rotating/moving mechanism 31 and the column rotating/moving mechanism 33. Referring to FIG. 2A showing the schematic arrangement of the C-arm rotating/moving mechanism 31 and the column rotating/moving mechanism 33, which are used to move the C-arm 5, the C-arm 5 is held on an arm holding unit 36 so as to be freely slid in a direction R2 by the C-arm rotating/moving mechanism 31. In addition, the arm holding unit 36 is held on the column 35 so as to be freely rotated about the body axis of subject P as a rotation axis in a direction R1 by the C-arm rotating/moving mechanism 31. Furthermore, the column 35 is held on a ceiling (not shown) so as to be rotated about the axis of the column 35 as a rotation axis in a direction R3 and translated in a longitudinal direction L1 and a widthwise direction L2 by the column rotating/moving mechanism 33.

As shown in FIG. 2B, the X-ray generating unit 1 and the X-ray detecting unit 2 rotate about a morbid region (e.g., the heart) of the subject P as a rotation center (isocenter) C0 of an X-ray beam in the first oblique direction (RAO) and the second oblique direction (LAO) upon rotation of the C-arm 5 as the arm holding unit 36 rotates in the direction R1.

As shown in FIG. 2C, the X-ray generating unit 1 and the X-ray detecting unit 2 rotate about the isocenter of the subject P in the cranial direction (CRA) and the caudal direction (CAU) as the C-arm 5 slides at a slide angle in the direction R2.

That is, the positions of the X-ray generating unit 1 and X-ray detecting unit 2 in directions RAO, LAO, CRA, and CAU as photographing conditions are set by rotation and sliding of the C-arm 5. This position setting makes it possible to perform X-ray fluoroscopy and imaging of the subject P from an arbitrary angle. In addition, the positions of the X-ray generating unit 1 and X-ray detecting unit 2 in the directions R3, L1, and L2 of column 35 are set.

The high voltage control unit 4 shown in FIG. 1 comprises a high voltage generator 41 which generates a high voltage to be applied between the anode and cathode of the X-ray tube 11 to accelerate thermoelectrons emitted from the cathode, and an X-ray control unit 42 which controls X-ray application conditions such as a tube current, tube voltage, and application time in a high voltage generator 41 in accordance with instruction signals from the system control unit 10.

The image data processing unit 7 comprises an image data generating unit 71 which generates various kinds of image data from X-ray projection data output from the X-ray detecting unit 2 on a line basis, and an image data storage unit 72 which holds image data generated by the image data generating unit 71.

The image data generating unit 71 has a function of generating fluoroscopic image data and sensed image data from X-ray projection data output from the X-ray detecting unit 2 on a line basis upon application of X-rays for fluoroscopy or imaging.

The image data generating unit 71 has a function of generating DA (Digital Angiography) image data from X-ray projection data obtained by application of X-rays for imaging in a state wherein a contrast medium is injected into a blood vessel of the subject P, and a function of generating DSA (Digital Subtraction Angiography) image data by difference processing between mask image data and contrast image data which are obtained from almost the same position as a photographing condition before and after the injection of a contrast medium into a blood vessel of the subject P.

In addition, the image data generating unit 71 has a function of generating fluoroscopic road map image data, in which a blood vessel image, a guide wire image, and the like are extracted, by performing subtraction processing between fluoroscopic image data generated by fluoroscopy of the subject P in which a guide wire is inserted into a blood vessel and reference image data generated at almost the same position as an imaging condition as that of the fluoroscopic image data.

Sensed image data generated by imaging and reference image data are stored in the image data storage unit 72 upon adding, to the image data, information concerting the image data, such as imaging conditions including the position information of operation units such as the filter of the compensating filter 12, the upper and lower blades of the X-ray stop 13, the C-arm 5, the top 17, and the column 35, and imaging time.

The display unit 8 displays image data such as fluoroscopic image data, reference image data, and fluoroscopic road map image data generated by the image data generating unit 71, which are read out from the image data storage unit 72, and also displays a window which is generated by the system control unit 10 and is used to set imaging conditions, operation conditions, and the like. The display unit 8 comprises a display data generating circuit which generates display data by combining these image data and numbers as accessory information thereof, various kinds of characters, and the like, a conversion circuit which generates a video signal by performing D/A conversion and TV format conversion with respect to the above image data and accessory information data, and a plurality of monitors such as a liquid crystal panel and a CRT which display the video signal.

The operating unit 9 comprises an operating unit 90 for hand operation and a foot switch unit 91 for foot operation. The operating unit 90 is an interactive interface comprising input devices such as a keyboard, trackball, joystick, and mouse, a display panel, various kinds of switches, and the like, and is used to set subject information, operation conditions for the foot switch unit 91, imaging conditions, and the like and input various kinds of commands.

The foot switch unit 91 comprises a plurality of pedal switches and button switches for foot operation. User instructions corresponding to actions such as generating X-rays, moving the C-arm 5, and displaying image data are input through these switches. In order to realize an action corresponding to a user instruction input through a switch which is turned on by being stepped on, the system control unit 10 controls the X-ray detecting unit 2, high voltage control unit 4, mechanical unit 3, and image data processing unit 7. This control will be described in detail later.

Assume that the C-arm 5 is set as an operation unit in advance, and first position A at which the X-ray generating unit 1 and the X-ray detecting unit 2 on the C-arm 5 are set at positions X11 and X21 shown in FIG. 2, and second position B at which the X-ray generating unit 1 and the X-ray detecting unit 2 are set at positions X12 and X22 are registered as two positions of the C-arm 5. In this case, when the foot switch unit 91 is operated by a foot to first position A, the C-arm 5 can be moved from home positions X10 and X20 to first position A, and image data can be displayed. When the foot switch unit 91 is operated by a foot to second position B, the C-arm 5 can be moved from first position A to second position B, and image data can be displayed.

The system control unit 10 comprises a CPU and a storage circuit 10a, and performs overall system control after temporarily storing information such as operator's commands supplied from the operating unit 9 and imaging conditions. Overall system control includes, for example, control associated with the movement of an operation unit, the generation of X-ray projection data, the generation and display of various kinds of image data, and the like based on these pieces of information.

The storage circuit 10a stores the correspondence between a plurality of foot switches of the foot switch unit 91 and a plurality of actions including at least one of the generation of X-rays and the movement of the C-arm 5.

Figure 3:
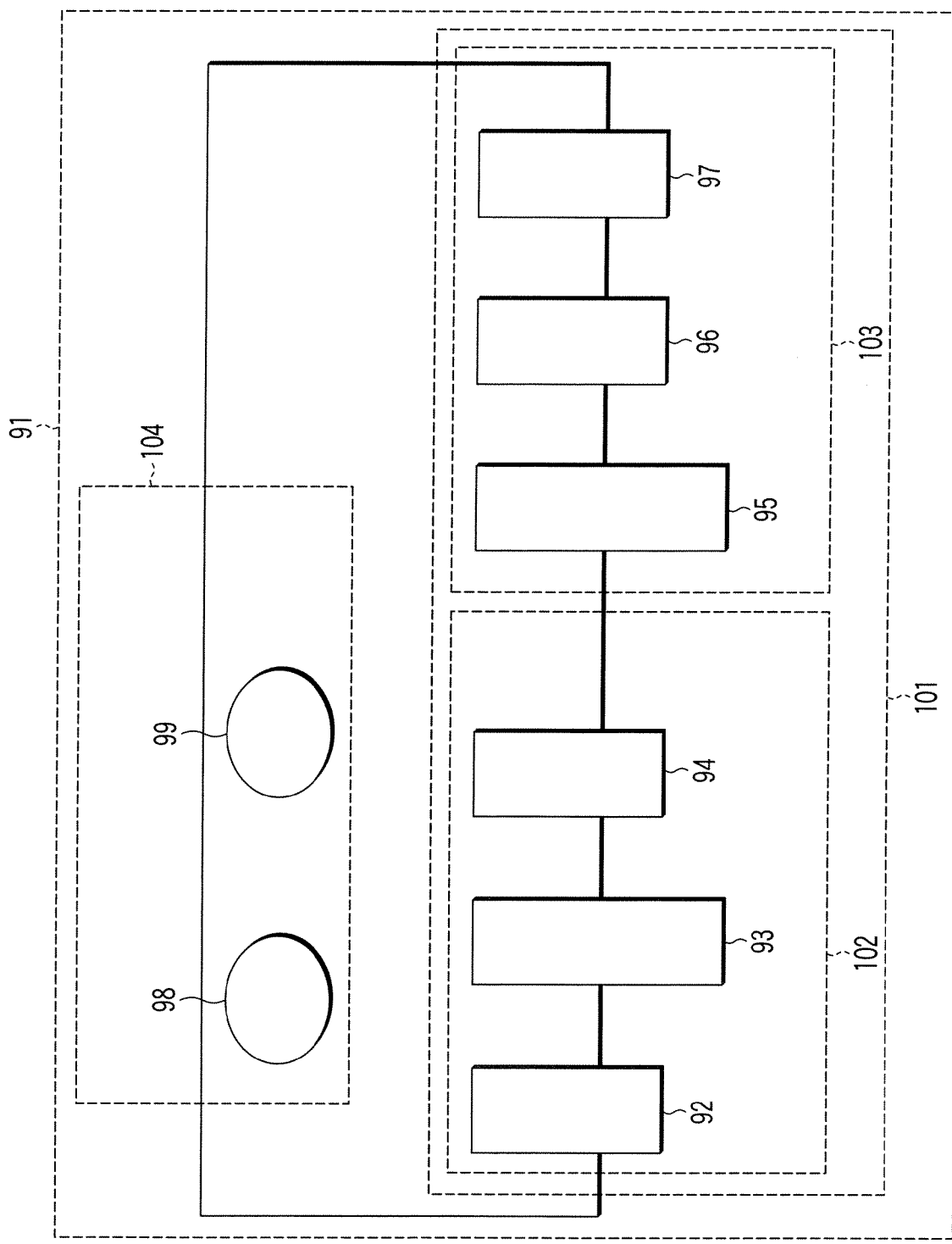
FIG. 3 is a view showing the arrangement of foot switches according to this embodiment.

The operation of the X-ray diagnostic apparatus 100 based on the operation of the foot switch unit 91 of the operating unit 9 will be described next with reference to FIGS. 1 to 8. FIG. 3 is a view showing the arrangement of the foot switch unit 91.

The foot switch unit 91 is placed on the floor and comprises an X-ray application operating unit 101 which operates for fluoroscopy and imaging operation, and a switching operating unit 104 which operates to switch operation patterns of fluoroscopy.

The X-ray application operating unit 101 comprises a fluoroscopy operating unit 102 which performs operation associated with fluoroscopy and an imaging operating unit 103 which performs operation associated with imaging operation.

The fluoroscopy operating unit 102 comprises a foot switch 92 for inputting a user instruction to move the C-arm 5 from first position A to second position B and display fluoroscopic image data and fluoroscopic road map image data at each position, a foot switch 94 for inputting a user instruction to move the C-arm 5 in the reverse direction to that corresponding to the foot switch 92 from position B to position A and display fluoroscopic image data and fluoroscopic road map image data at each position, and a foot switch 93 for inputting a user instruction to acquire and display fluoroscopic image data upon continuous generation of X-rays. The foot switch 93 is placed between the foot switches 92 and 94 corresponding to the movement of the C-arm 5.

The imaging operating unit 103 comprises an imaging switch 95 for performing imaging operation of generating a higher dose of X-rays than for fluoroscopic corresponding to the foot switch 93 by one shot, a moving imaging switch 96 for performing imaging operation while moving the C-arm 5 from first position A to second position B, and a position imaging switch 97 for performing imaging operation at each of first position A and second position B. The imaging switch 95 is placed outside foot switches 92, 93, and 94 for fluoroscopy. The switches 96 and 97 are arranged outside the imaging switch 95. In order to prevent operation errors, the distance between the imaging switch 95 and the foot switch 94 is preferably designed to be longer than the distance between the fluoroscopy switches 92 and 93 and the distance between the fluoroscopy switches 93 and 94. In addition, a partition wall is provided between the imaging switch 95 and fluoroscopy switch 94.

Each of the switches of the fluoroscopy operating unit 102 and imaging operating unit 103 of the X-ray application operating unit 101 is ON while being pressed, and is OFF while being released. When a plurality of switches are simultaneously pressed, none of the switches is turned on.

The switching operating unit 104 comprises a fluoroscopic road map/fluoroscopy switch 98 which comprises foot buttons and is ON/OFF-operated to select fluoroscopic road map image data and fluoroscopic image data before the foot switch 92 and the foot switch 94 are operated, and an interlocking switch 99 which is ON/OFF-operated to select whether to apply X-ray for fluoroscopy from the operation unit.

Once each of the fluoroscopic road map/fluoroscopy switch 98 and interlocking switch 99 of the switching operating unit 104 is turned on or off, the state of the switch is maintained until it is pressed next.

LEDs (not shown) which are lighted on/off as the switches of the foot switch unit 91 are turned on/off are arranged adjacent to the respective switches. Icons corresponding to the respective LEDs are displayed on the display unit 8.

Figure 4:
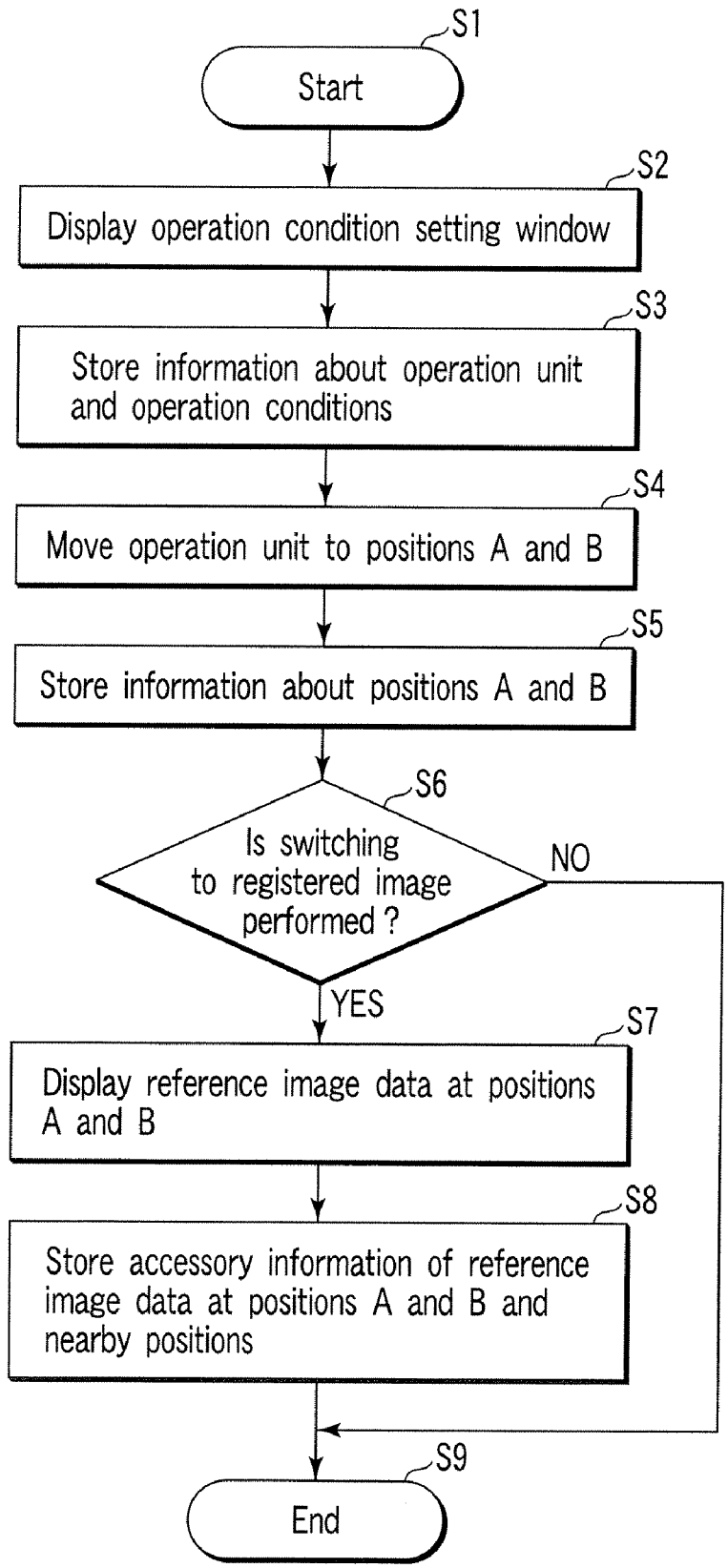
FIG. 4 is a flowchart showing a sequence for setting operation conditions in a foot switch unit 91 according to this embodiment.

FIG. 4 is a flowchart showing a sequence for setting operation conditions for the foot switch unit 91. First of all, when operation condition setting window display operation is performed by using the operating unit 90 of the operating unit 9, the X-ray diagnostic apparatus 100 starts operation condition registering operation (step S1). The system control unit 10 causes display unit 8 to display an operation condition setting window (step S2).

FIG. 5 is a view showing a preset window for presetting operation conditions. A preset window 120 is generated by the system control unit 10 in response to operation of the operating unit 90 as a trigger, and comprises an automatic positioning unit setting area 124 for setting an operation unit, a holding device registration information setting area 123 for setting an operation unit which registers the position of the operation unit, a fluoroscopy/automatic positioning setting area 121 for setting operation conditions for the set operation unit and execution/non-execution of fluoroscopy, and a reference image display/automatic positioning setting area 122 for setting movement (automatic positioning) from first position A to second position B and execution/non-execution of display of reference image data.

Operation conditions are set in the preset window 120 by using the display panel, keyboard, mouse, and the like of the operating unit 90. When portions of circle and rectangular frames are clicked, bullets and checks are displayed and set in the circle and rectangular frames.

In the automatic positioning unit setting area 124, the following are displayed: "C-arm rotational angle/C-arm slide angle", "SID", "detector rotational angle", "column longitudinal position/widthwise position", "column angle", "X-ray stop aperture position", "filter position", "bed position information", "top height", "top longitudinal position", "top widthwise position", "top rotational angle", and the like corresponding to operation units such as the C-arm 5, the X-ray flat panel detector 21, the column 35, the upper and lower blades of the X-ray stop 13, the filter of the compensating filter 12, and the top 17. In this case, for example, only "arm rotational angle/arm slide angle" is set.

In the holding device registration information setting area 123, the same operation units as those in the automatic positioning unit setting area 124 are displayed, and an operation unit whose position is to be registered is set. In this case, for example, only "arm rotational angle/arm slide angle" is set.

On the upper side of the fluoroscopy/automatic positioning setting area 121, "only automatic positioning is executed" and "fluoroscopy and automatic positioning are executed" are displayed. When "fluoroscopy and automatic positioning are executed" is set, one of the following displayed on the lower side is selected and set: "fluoroscopic is always performed while SW is ON", "fluoroscopy is performed upon completion of automatic positioning", and "fluoroscopy is started before completion of automatic positioning".

When "only automatic positioning is executed" is set, the operation unit moves from first position A to second position B.

When "fluoroscopy and automatic positioning are executed" and "fluoroscopy is always performed while SW is ON" are set, the operation unit starts to move to first position A and second position B, and fluoroscopic image data is generated and displayed on the display unit 8.

When "fluoroscopy and automatic positioning are executed" and "fluoroscopy is performed upon completion of automatic positioning" are set, fluoroscopic image data at first position A and second position B are generated and displayed on the display unit 8 at the time points at which the operation unit reaches first position A and second position B.

When "fluoroscopy and automatic positioning are executed" and "fluoroscopy is started before completion of automatic positioning" are set, fluoroscopic image data is generated and displayed on display unit 8 a predetermined period of time before the set operation unit reaches first position A and second position B.

In this case, for example, "fluoroscopy and automatic positioning are executed" and "fluoroscopy is performed upon completion of automatic positioning" are set.

On the upper side of the reference image display/automatic positioning setting area 122, "automatic display of reference image is performed" is displayed. When "automatic display of reference image is performed" is set, one of the following displayed on the lower side is selected: "switching to registered image is performed" and "automatic search is made from acquired images".

Assume that "automatic display of reference image is performed" and "switching to registered image is performed" are set. In this case, if "only automatic positioning is executed" in the fluoroscopy/automatic positioning setting area 121 has been set, the operation unit starts to move to first position A and second position B, and reference image data registered in advance for first position A and second position B are displayed on the display unit 8.

In addition, if "fluoroscopy and automatic positioning are executed" on the upper side of the fluoroscopy/automatic positioning setting area 121 has been set, reference image data registered for first position A and second position B are displayed on the display unit 8 at the same timings as the fluoroscopic image data display timings set for "fluoroscopy is always performed while SW is ON", "fluoroscopy is performed upon completion of automatic positioning", and "fluoroscopy is started before completion of automatic positioning" on the lower side.

When "automatic display of reference image is performed" and "automatic search is made from acquired images" are set, the image data storage unit 72 of the image data processing unit 7 is searched for reference image data having accessory information indicating that a position as a photographing condition for the operation unit falls within a predetermined range, and the found data is displayed on the display unit 8 at the same timing as the condition set in the fluoroscopy/automatic positioning setting area 121 of "switching to registered image is performed". If, for example, the operation unit is the C-arm 5, a search is made for reference image data indicating that the rotational angle and slide angle fall within ±5° with respect to, for example, first position A and second position B. If a plurality of reference image data are found, reference image data closest to first position A and second position B is displayed on the display unit 8.

Note that the image data generating unit 71 generates fluoroscopic road map image data using reference image data set in this area by operating the foot switch unit 91.

Assume that "automatic display of reference image is performed" and "switching to registered image is performed" are set.

Note that the preset window 120 has a plurality of windows, and setting operation units and operation conditions in the plurality of windows in advance allows selection thereof for each diagnosis or medical treatment. The types of operation units are not limited to those displayed in the preset window 120, and vary depending on the operation units of various kinds of X-ray diagnostic apparatuses.

The system control unit 10 stores, in the storage circuit 10a, the operation conditions set in the preset window 120 of the display unit 8 by operation condition setting operation of the operating unit 90 of the operating unit 9 (step S3 in FIG. 4).

In order to register the position of each operation unit set in the preset window 120, the position setting operation of operating unit 90 is performed for the operation unit, and each operation unit is moved to first position A and second position B (step S4 in FIG. 4). First position A and second position B are registered by using the operating unit 90, and the system control unit 10 stores, in the storage circuit 10a, information of first position A and information of second position B of each operation unit which are respectively set at first position A and second position B (step S5 in FIG. 4).

When "switching to registered image is performed" is set in the reference image display/automatic positioning setting area 122 in the preset window 120 (YES in step S6 in FIG. 4), the operator performs search operation for registering reference image data, of reference image data stored in the image data storage unit 72, which are sensed at first position A and second position B or their nearby positions for first position A and second position B. In addition, if "switching to registered image is performed" is not set (NO in step S6 in FIG. 4), the flow advances to step S9.

When display operation for reference images for first position A and second position B is performed with the operating unit 90, the image data generating unit 71 reads out reference image data for first position A and second position B from the image data storage unit 72 and displays them on the display unit 8 (step S7 in FIG. 4).

In addition, when registering operation for reference images for first position A and second position B is performed with the operating unit 90 with respect to the reference image data displayed on the display unit 8, the system control unit 10 stores the accessory information of reference image data for first position A and second position B which are displayed on the display unit 8 in the storage circuit 10a in association with first position A and second position B (step S8 in FIG. 4). The X-ray diagnostic apparatus 100 then terminates the operation condition registering operation (step S9 in FIG. 4).

Operation patterns 1 to 10 performed with the foot switch unit 91 of the X-ray diagnostic apparatus 100 will be described next with reference to FIGS. 6A, 6B, 6C, 7A, 7B, 7C, and 7D. Assume that operation is performed in accordance with the operation unit and operation conditions set in the preset window 120 in FIG. 5. Therefore, the C-arm 5 operates in accordance with the operation of the foot switch unit 91, and the operation units other than the C-arm 5 are set at predetermined positions by the operation of the operating unit 90.

Figure 6C:
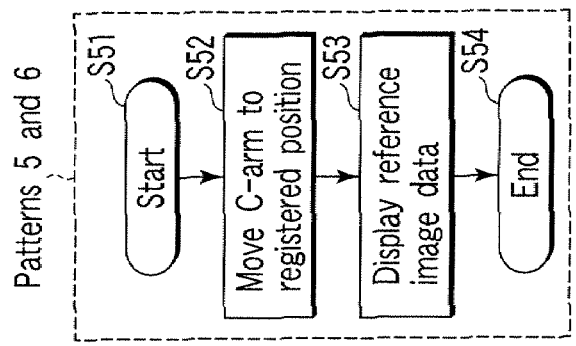
FIG. 6C is a flowchart showing a sequence for operation patterns 5 and 6 according to this embodiment.
Figure 6B:
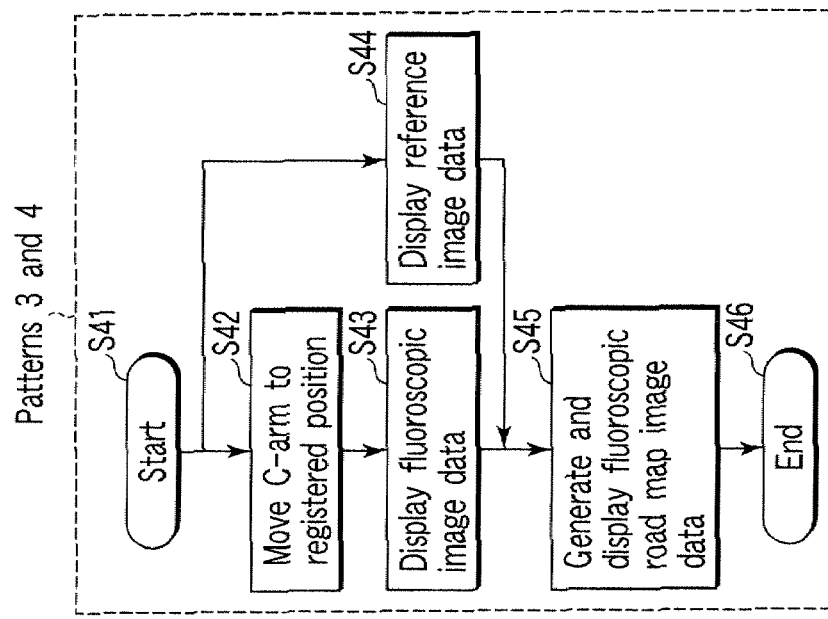
FIG. 6B is a flowchart showing a sequence for operation patterns 3 and 4 according to this embodiment.
Figure 6A:
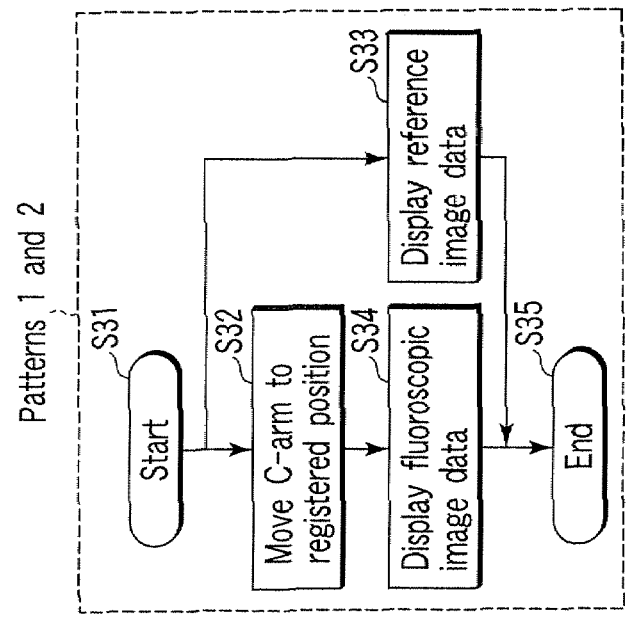
FIG. 6A is a flowchart showing a sequence for operation patterns 1 and 2 according to this embodiment.

FIG. 6A is a flowchart showing the operation of pattern 1 in moving an operation unit and displaying image data. The operation of pattern 1 will be described first. When the foot switch 92 of the fluoroscopy operating unit 102 is stepped on to be turned on while the fluoroscopic road map/fluoroscopy switch 98 of the switching operating unit 104 of the foot switch unit 91 is OFF and the interlocking switch 99 is ON, the X-ray diagnostic apparatus 100 starts the operation of pattern 1 (step S31).

The system control unit 10 gives instructions to the mechanical unit 3, high voltage control unit 4, X-ray generating unit 1, X-ray detecting unit 2, image data processing unit 7, and display unit 8 to perform the operation of pattern 1. The C-arm rotating/moving mechanism 31 of the mechanical unit 3 continuously moves the C-arm 5 from the home position to registered first position A under the control of the C-arm/top mechanism control unit 34 while the foot switch 92 is stepped on (step S32). When the foot switch 92 is released, the C-arm 5 stops. When the C-arm 5 reaches first position A, the movement of the C-arm 5 automatically stops, and reference image data at first position A is displayed on the display unit 8.

The image data generating unit 71 reads out reference image data registered in association with first position A from the image data storage unit 72 under the control of the system control unit 10 when the C-arm 5 reaches first position A, and displays the reference image data on the display unit 8 (step S33).

When the C-arm 5 reaches first position A, the X-ray generating unit 1 generates X-rays upon application of a voltage for fluoroscopy from the high voltage control unit 4. The X-rays are applied to the subject P. The X-ray detecting unit 2 generates X-ray projection data from the detected X-rays and outputs the data to the image data generating unit 71 of the image data processing unit 7. The image data generating unit 71 generates fluoroscopic image data from the X-ray projection data output from the X-ray detecting unit 2 and displays the generated data on the display unit 8 (step S34).

When the operator releases his/her foot from the foot switch 92 to turn it off, the X-ray diagnostic apparatus 100 terminates the operation of pattern 1 (step S35).

The operation of pattern 2 differs from that of pattern 1 in that the foot switch 94 of the fluoroscopy operating unit 102 is turned on while the fluoroscopic road map/fluoroscopy switch 98 is OFF and the interlocking switch 99 is ON. With this operation, the X-ray diagnostic apparatus 100 starts the operation of pattern 2 (step S31).

Likewise, subsequently, the system control unit 10 gives instructions to the mechanical unit 3, high voltage control unit 4, X-ray generating unit 1, X-ray detecting unit 2, image data processing unit 7, and display unit 8 to perform the operation of X-ray detecting unit 2. The C-arm rotating/ moving mechanism 31 of mechanical unit 3 continuously moves the C-arm 5 to second position B under the control of the C-arm/top mechanism control unit 34 while the foot switch 94 is stepped on (step S32). When the foot switch 94 is released, the C-arm 5 stops. When the C-arm 5 reaches second position B, the movement of the C-arm 5 automatically stops, and reference image data at second position B is displayed on the display unit 8.

The image data generating unit 71 reads out the reference image data registered in association with second position B from the image data storage unit 72 and displays the data on the display unit 8 under the control of the system control unit 10 when the C-arm 5 reaches first position (step S33).

When the C-arm 5 reaches second position B, the X-ray generating unit 1 generates X-rays upon application of a voltage for fluoroscopy from the high voltage control unit 4. The X-rays are applied to subject P. The X-ray detecting unit 2 generates X-ray projection data from the detected X-rays and outputs the data to the image data generating unit 71 of the image data processing unit 7. The image data generating unit 71 generates fluoroscopic image data from the X-ray projection data output from the X-ray detecting unit 2 and displays the generated data on the display unit 8 (step S34).

When the operator releases his/her foot from the foot switch 94 to turn it off, the X-ray diagnostic apparatus 100 terminates the operation of pattern 2 (step S35).

The operations of patterns 3 and 4 will be described next. The operation of pattern 3 will be described first. When the foot switch 92 of the fluoroscopy operating unit 102 is turned on while the fluoroscopic road map/fluoroscopy switch 98 and the interlocking switch 99 of the switching operating unit 104 of the foot switch unit 91 are ON, the X-ray diagnostic apparatus 100 starts the operation of pattern 3 (step S41).

The system control unit 10 gives instructions to the mechanical unit 3, high voltage control unit 4, X-ray generating unit 1, X-ray detecting unit 2, image data processing unit 7, and display unit 8 to perform the operation of pattern 3. The C-arm rotating/moving mechanism 31 continuously moves the C-arm 5 from the home position to first position A under the control of the C-arm/top mechanism control unit 34 while the foot switch 92 is stepped on (step S42). When the foot switch 92 is released, the C-arm 5 stops. When the C-arm 5 reaches first position A, the movement of the C-arm 5 automatically stops.

When the C-arm 5 reaches first position A, the X-ray generating unit 1 generates X-rays upon application of a voltage for fluoroscopy from the high voltage control unit 4. The X-ray detecting unit 2 generates X-ray projection data from the detected X-rays and outputs the data to the image data generating unit 71 of the image data processing unit 7. The image data generating unit 71 generates fluoroscopic image data from the X-ray projection data output from the X-ray detecting unit 2 (step S43).

In addition, the image data generating unit 71 reads out the reference image data registered at first position A from the image data storage unit 72 (step S44).

Furthermore, the image data generating unit 71 generates fluoroscopic road map image data from the fluoroscopic image data generated at first position A and the read reference image data and displays the generated data on the display unit 8 (step S45). When the foot switch 92 is turned off, the X-ray diagnostic apparatus 100 terminates the operation of pattern 3 (step S46).

As shown in FIG. 6B, in the operation of pattern 4, the foot switch 94 of the fluoroscopy operating unit 102 is stepped on to be turned on instead of the foot switch 92 described with reference to pattern 3. While the foot switch 94 is stepped on, the C-arm 5 continuously moves to second position B. When the foot switch 94 is released, the C-arm 5 stops. When the C-arm 5 reaches second position B, fluoroscopic road map image data at second position B can be generated and displayed on the display unit 8.

The operations of patterns 5 and 6 will be described next. Pattern 5 will be described first. As shown in FIG. 6C, when the foot switch 92 is turned on while the interlocking switch 99 of the foot switch unit 91 is OFF, the X-ray diagnostic apparatus 100 starts the operation of pattern 5 regardless of whether the fluoroscopic road map/fluoroscopy switch 98 is turned on/off (step S51).

The system control unit 10 gives instructions to the mechanical unit 3, image data processing unit 7, and display unit 8 to perform the operation of pattern 5. The C-arm rotating/moving mechanism 31 moves the C-arm 5 to first position A under the control the C-arm/top mechanism control unit 34 (step S52).

When the C-arm 5 reaches first position A, the image data generating unit 71 reads out the reference image data registered in association with first position A from the image data storage unit 72 and displays the data on the display unit 8 (step S53). When the foot switch 92 is turned off, the X-ray diagnostic apparatus 100 terminates the operation of pattern 5 (step S54).

As shown in FIG. 6C, in the operation of pattern 6, the foot switch 94 is turned on instead of the foot switch 92 described with reference to pattern 5. While the foot switch 94 is stepped on, the C-arm 5 continuously moves to second position B. When the C-arm 5 reaches second position B, the movement of the C-arm 5 stops, and the reference image data at second position B is displayed on the display unit 8.

Performing the operations of patterns 1 and 2 with the operation of the foot switch unit 91 in this manner makes it possible to move an operation unit such as the C-arm 5 to first position A and second position B and display fluoroscopic image data and reference image data at each position on the display unit 8. Alternately performing the operations of pattern 1 and pattern 2 makes it possible to alternately move an operation unit from first position A to second position B and from second position B to first position A and display fluoroscopic image data and reference image data at the respective positions on the display unit 8 when the operation unit reaches the respective positions.

In addition, by performing the operations of patterns 3 and 4, when an operation unit such as the C-arm 5 moves to first position A and second position B and reach them, fluoroscopic road map image data at each position can be displayed on the display unit 8. By alternately performing the operations of patterns 3 and 4, when an operation unit alternately moves from first position A to second position B and from second position B to first position A to reach each position, fluoroscopic road map image data at each position can be displayed on the display unit 8.

In addition, by performing the operations of patterns 5 and 6, when an operation unit such as the C-arm 5 moves to first position A and second position B to reach them, reference image data at each position can be displayed on the display unit 8. By alternately performing the operations of patterns 5 and 6, when an operation unit alternately moves from first position A to second position B and from second position B to first position A to reach them, reference image data at each position can be displayed on the display unit 8.

Note that an arbitrary operation unit other than a unit for C-arm rotational angle/C-arm slide angle can be moved to first position A and second position B by setting the arbitrary operation unit and registering the position of the operation unit at first position A and second position B in the automatic positioning unit setting area 124 and the holding device registration information setting area 123 in the preset window 120, as needed.

The display timings of fluoroscopic image data, reference image data, and fluoroscopic road map image data can be displayed on the display unit 8 before an operation unit reaches first position A and second position B by setting "fluoroscopy and automatic positioning are executed" and "fluoroscopy is started before completion of automatic positioning" in the fluoroscopy/automatic positioning setting area 121 in the preset window 120.

FIGS. 7A, 7B, 7C, and 7D are flowcharts showing the operations of pattern 7 to 10 in moving an operation unit and performing fluoroscopy/imaging operation. The operation of pattern 7 will be described first. As shown in FIG. 7A, when the foot switch 93 of the fluoroscopy operating unit 102 of the foot switch unit 91 is turned on, the X-ray diagnostic apparatus 100 starts the operation of the pattern 7 (step S71).

The system control unit 10 gives instructions to the high voltage control unit 4, X-ray generating unit 1, X-ray detecting unit 2, image data processing unit 7, and display unit 8 to perform the operation of pattern 7.

The high voltage control unit 4 continuously applies a high voltage for fluoroscopy to the X-ray generating unit 1 while the fluoroscopy switch 93 is stepped on. With this operation, X-rays are continuously generated. The X-ray detecting unit 2 generates X-ray projection data from detected X-rays and outputs the data to the image data generating unit 71 of the image data processing unit 7. The image data generating unit 71 generates fluoroscopic image data from the X-ray projection data output from the X-ray detecting unit 2 and displays the generated data on the display unit 8 (step S72). When the fluoroscopy switch 93 is turned off, the X-ray diagnostic apparatus 100 terminates the operation of pattern 7 (step S73).

By performing the operation of pattern 7 with the operation of the foot switch unit 91 in this manner, fluoroscopic image data at the position corresponding to the time when the fluoroscopy switch 93 is turned on can be displayed on the display unit 8.

The operation of pattern 8 will be described next. As shown in FIG. 7B, when the moving imaging switch 96 of the imaging operating unit 103 of the foot switch unit 91 is stepped on to be turned on, the X-ray diagnostic apparatus 100 starts the operation of pattern 8 (step S81).

The system control unit 10 gives instructions to the mechanical unit 3, high voltage control unit 4, X-ray generating unit 1, X-ray detecting unit 2, image data processing unit 7, and display unit 8 to perform the operation of pattern 8. The C-arm rotating/moving mechanism 31 moves the C-arm 5 from the home position to first position A and then moves the C-arm 5 to second position B through the shortest distance under the control of the C-arm/top mechanism control unit 34 (step S82).

The X-ray generating unit 1 applies X-rays to the subject P upon application of a voltage for imaging operation from the high voltage control unit 4 while the C-arm 5 moves from first position A and reaches second position B. The X-ray detecting unit 2 generates X-ray projection data from detected X-rays and outputs the data to the image data generating unit 71 of the image data processing unit 7. The image data generating unit 71 generates fluoroscopic image data from the X-ray projection data output from the X-ray detecting unit 2 and displays the generated data on the display unit 8 (step S83).

When the C-arm 5 reaches second position B, the X-ray diagnostic apparatus 100 terminates the operation of pattern 8 (step S84).

Performing the operation of pattern 8 with the operation of the foot switch unit 91 in this manner makes it possible to perform imaging operation while moving an operation unit such as the C-arm 5 from first position A to second position B and store and display sensed image data generated during the imaging operation.

The operation of pattern 9 will be described next. As shown in FIG. 7C, when the position imaging switch 97 of the imaging operating unit 103 of the foot switch unit 91 is turned on, the X-ray diagnostic apparatus 100 starts the operation of pattern 9 (step S91).

The system control unit 10 gives instructions to the mechanical unit 3, high voltage control unit 4, X-ray generating unit 1, X-ray detecting unit 2, and image data processing unit 7 to perform the operation of pattern 9. The C-arm rotating/moving mechanism 31 moves the C-arm 5 to first position A under the control of the column rotating/moving mechanism 33 (step S92).

The X-ray generating unit 1 applies X-rays to the subject P upon application of a voltage for imaging operation from the high voltage control unit 4 when the C-arm 5 reaches first position A. The X-ray detecting unit 2 generates X-ray projection data from detected X-rays and outputs the data to the image data generating unit 71 of the image data processing unit 7. The image data generating unit 71 generates sensed image data at first position A from the X-ray projection data output from the X-ray detecting unit 2 and stores the generated data in the image data storage unit 72 (step S93).

The C-arm rotating/moving mechanism 31 then moves the C-arm 5 to second position B under the control of the column rotating/moving mechanism 33 (step S94).

When the C-arm 5 reaches second position B, the X-ray generating unit 1 applies X-rays to the subject P upon application of a voltage for imaging operation from the high voltage control unit 4. The X-ray detecting unit 2 generates X-ray projection data from detected X-rays and outputs the data to the image data generating unit 71 of the image data processing unit 7. The image data generating unit 71 generates sensed image data at second position B from the X-ray projection data output from the X-ray detecting unit 2 and stores the generated data in the image data storage unit 72 (step S95). The X-ray diagnostic apparatus 100 then terminates the operation of pattern 9 (step S96).

Performing the operation of pattern 9 with the operation of the foot switch unit 91 in this manner makes it possible to move an operation unit such as the C-arm 5 to first position A and second position B and store sensed image data generated at each position when the C-arm 5 reaches it.

The operation of pattern 10 will be described next. As shown in FIG. 7D, when the imaging switch 95 of the foot switch unit 91 is turned on, the X-ray diagnostic apparatus 100 starts the operation of pattern 10 (step S101). The system control unit 10 gives instructions to the high voltage control unit 4, X-ray generating unit 1, X-ray detecting unit 2, and image data processing unit 7 to perform the operation of pattern 10.

The X-ray generating unit 1 applies X-rays to the subject P upon application of a voltage for imaging operation from the high voltage control unit 4. The X-ray detecting unit 2 generates X-ray projection data from detected X-rays and outputs the data to the image data generating unit 71 of the image data processing unit 7. The image data generating unit 71 generates sensed image data from the X-ray projection data output from the X-ray detecting unit 2 and stores the generated data in the image data storage unit 72 (step S102).

When the imaging switch 95 is turned off, the X-ray diagnostic apparatus 100 stops the operation of pattern 10 (step S103).

Performing the operation of pattern 10 with the operation of the foot switch unit 91 in this manner makes it possible to store, in the image data storage unit 72, the sensed image data generated at the position corresponding to the time when the imaging switch 95 is turned on.

Note that when the fluoroscopy operating unit 102 or the imaging operating unit 103 of the foot switch unit 91 is turned off during the movement of the operation unit after the start of the operation of each of patters 1 to 10, the operation of each pattern is temporarily stopped. When the switch which has been turned off is turned on, the operation is resumed from the position where the operation unit has temporarily stopped.

In addition, when the fluoroscopy switch 93 or the imaging switch 95 is turned on after the fluoroscopy operating unit 102 or imaging operating unit 103 of the foot switch unit 91 is turned off during the movement of the operation unit, fluoroscopy or imaging operation is resumed at the position where the operation unit has temporarily stopped.

When a reset button (not shown) of the foot switch unit 91 is pressed after the fluoroscopy operating unit 102 or the imaging operating unit 103 is turned off, the operation unit returns to a predetermined initial position. When the switch of the fluoroscopy operating unit 102 or the imaging operating unit 103 is turned on afterward, operation is started from the initial position.

Figure 8:
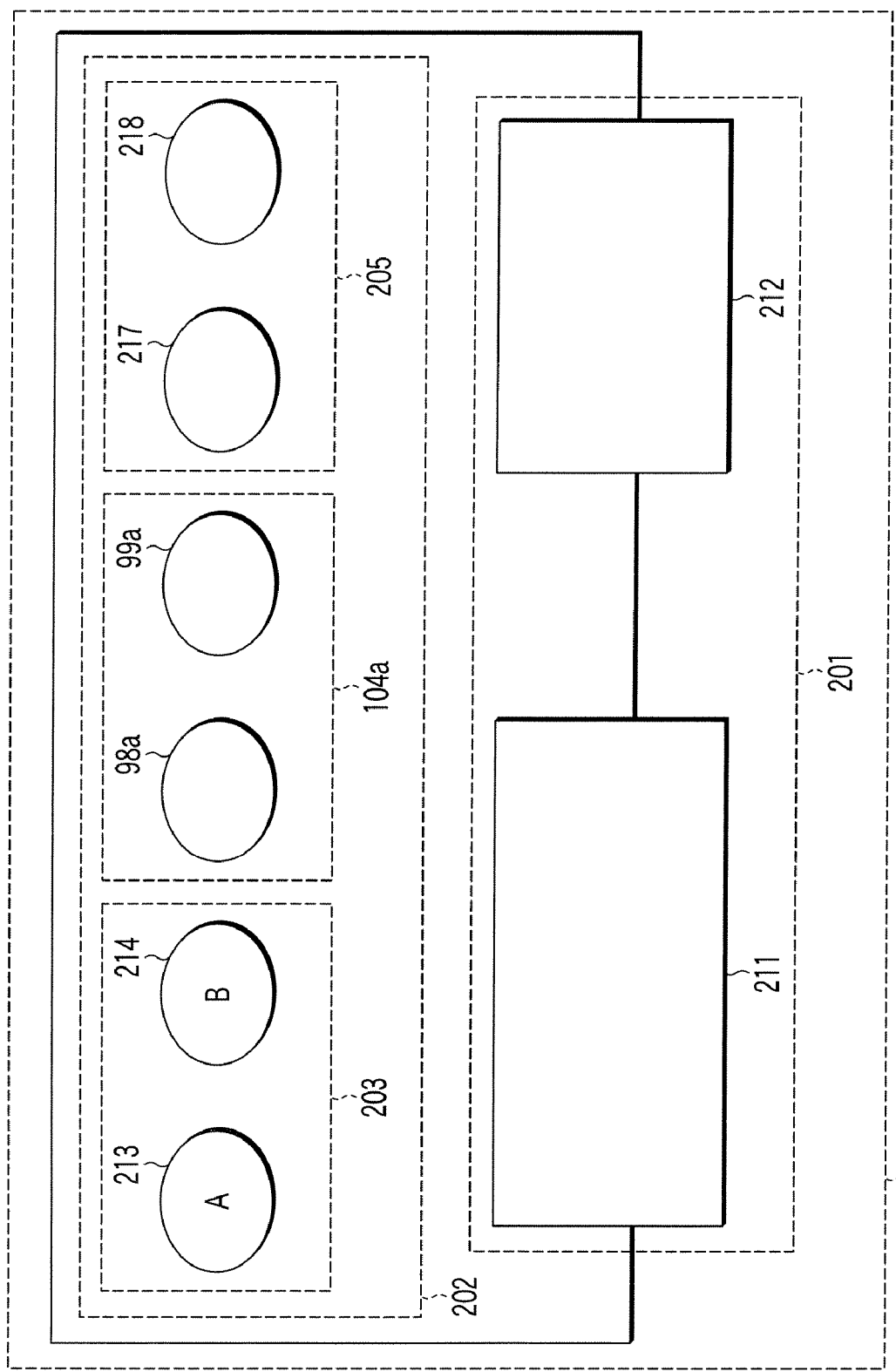
FIG. 8 is a view showing a modification of the foot switch according to this embodiment.

FIG. 8 shows another embodiment of a foot switch. A foot switch 200 differs from the foot switch unit 91 in FIG. 3 in that it is provided with a larger number of foot buttons than in the third embodiment in FIG. 3, and the respective switches have different functions. Since the respective switches have different functions, different switching operations are performed for the operations of patterns 1 to 10.

The foot switch 200 comprises an X-ray application operation unit 201 which performs fluoroscopy and imaging operation by applying X-rays and a switching operation unit 202 which selects the position of fluoroscopy, the type of image data to be displayed, and an operation pattern for imaging operation, and performs operation based on the combination of an X-ray application operation unit 201 and a switching operation unit 202.

The X-ray application operation unit 201 comprises two pedals, namely a fluoroscopy switch 211 for performing fluoroscopy and an imaging switch 212 for performing imaging operation. Each switch is ON while being pressed. When the two switches are simultaneously pressed, none of the switches is turned on.

The switching operation unit 202 comprises a position switching operation unit 203 which selects the position of fluoroscopy, a fluoroscopy switching operation unit 104*a* which selects an operation pattern for fluoroscopy, and an imaging switching operation unit 205 which selects an operation pattern for imaging operation. Each unit comprises foot buttons. Once a switch of each switching operation unit of the switching operation unit 202 is pressed, the ON state is maintained. When each switch is turned off, the OFF state is maintained until the switch is pressed next. The two switches of each switching operation unit cannot be simultaneously turned on.

The position switching operation unit 203 comprises a position A switch 213 and a position B switch 214 which select first position A and second position B at which fluoroscopy is to be performed. These switches are labeled "A" and "B".

The fluoroscopy switching operation unit 104*a* comprises a fluoroscopic road map/fluoroscopy switch 98*a* which selects fluoroscopic road map image data and fluoroscopic image data by ON/OFF operation and an interlocking switch 99*a* which selects, by ON/OFF operation, whether to make an operation unit apply X-rays for fluoroscopy.

The imaging switching operation unit 205 comprises a moving imaging switch 217 for performing imaging operation during movement from first position A to second position B and a position imaging switch 218 for performing imaging operation at first position A and second position B.

The operation of the foot switch 200 for the execution of the operations of patterns 1 to 10 shown in FIGS. 6A to 6C and FIGS. 7A to 7D will be described next.

The operation of pattern 1 is executed when the fluoroscopy switch 211 is turned on while the position A switch 213 and the interlocking switch 99*a* are ON.

The operation of pattern 2 is executed when the fluoroscopy switch 211 is turned on while the position B switch 214 and the interlocking switch 215 are ON.

The operation of pattern 3 is executed when the fluoroscopy switch 211 is turned on while the position A switch 213 and the fluoroscopic road map/fluoroscopy switch 216 are ON.

The operation of pattern 4 is executed when the fluoroscopy switch 211 is turned on while the position B switch 214 and the fluoroscopic road map/fluoroscopy switch 216 are ON.

The operation of pattern 5 is executed when the fluoroscopy switch 211 is turned on while the position A switch 213 is ON and the interlocking switch 215 is OFF.

The operation of pattern 6 is executed when the fluoroscopy switch 211 is turned on while the position B switch 214 is ON and the interlocking switch 215 is OFF.

The operation of pattern 7 is executed when the fluoroscopy switch 211 is turned on while the position A switch 213 and the position B switch 214 are OFF.

The operation of pattern 8 is executed when the imaging switch 212 is turned on while the moving imaging switch 217 is ON.

The operation of pattern 9 is executed when the imaging switch 212 is turned on while the position imaging switch 218 is ON.

The operation of pattern 10 is executed when the imaging switch 212 is turned on while the moving imaging switch 217 and the position imaging switch 218 are OFF.

According to the this embodiment described above, the operating foot switch unit 91 makes it possible to move an operation unit such as the C-arm 5 to first position A and second position B and display fluoroscopic image data and reference image data at each position, fluoroscopic road map image data at each position, and reference image data at each position on the display unit 8.

Since observation from two positions can be quickly performed without requiring manual operation by operating the foot switch unit 91 in this manner, an operator who often manually operates a catheter, a guide wire, and the like can quickly perform diagnosis or medical treatment.

In addition, operating foot switch unit 91 makes it possible to move an operation unit such as C-arm 5 to first position A and second position B and store sensed image data at each position. Furthermore, sensed image data can be stored while an operation unit such as C-arm 5 moves from first position A to second position B.

Since imaging at two positions and imaging between two positions can be easily performed by operating the foot switch unit 91 in this manner, an operator who often manually operates a catheter, a guide wire, and the like can quickly perform imaging operation at an observation region of a subject during diagnosis or medical treatment.

Note that the present invention is not limited to the above embodiment, and may be executed such that three or more positions are registered in advance and a foot switch is provided with switches which can perform operation at three positions or more.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus, comprising:
an X-ray generating unit which generates X-rays;
an X-ray detecting unit which detects X-rays transmitted through a subject;
a C-arm on which the X-ray generating unit and the X-ray detecting unit are mounted;
a support mechanism which movably supports the C-arm;
a high voltage generating unit which generates a high voltage for generating X-rays from the X-ray generating unit;
a first foot switch to input a first user instruction associated with generation of the X-rays;
a second foot switch to input a second user instruction associated with movement of the C-arm;
a control unit which controls the high voltage generating unit in accordance with the input of the first user instruction and controls the support mechanism in accordance with the input of the second user instruction; and
a third foot switch to input a third user instruction associated with movement of the C-arm in a direction opposite to that corresponding to the second user instruction,
wherein the first foot switch is placed between the second foot switch and the third foot switch.

2. An apparatus according to claim 1, further comprising a fourth foot switch to input a fourth user instruction associated with generation of a higher dose of X-rays than that corresponding to the first user instruction.

3. An apparatus according to claim 2, wherein the fourth foot switch is placed outside the first foot switch, the second foot switch, and the third foot switch.

4. An apparatus according to claim 2, wherein the control unit controls the high voltage generating unit to generate X-rays by one shot when the fourth foot switch is stepped on.

5. An apparatus according to claim 1, wherein the control unit controls the high voltage generating unit to continuously generate X-rays while the first foot switch is stepped on.

6. An apparatus according to claim 1, wherein the control unit controls the support mechanism to continuously move the C-arm while the second foot switch is stepped on.

7. An apparatus according to claim 6, wherein the control unit controls the support mechanism to stop the C-arm when the second foot switch is released.

8. An apparatus according to claim 6, wherein the control unit controls the support mechanism to stop the C-arm at a predetermined position when the C-arm reaches the predetermined position.

9. An apparatus according to claim 6, wherein the control unit controls the support mechanism to stop the C-arm at a predetermined position when the C-arm reaches the predetermined position, and controls the high voltage generating unit to start generation of the X-rays.

10. An apparatus according to claim 6, wherein the control unit controls the support mechanism to stop the C-arm at a predetermined position when the C-arm reaches the predetermined position, and controls the high voltage generating unit to start generation of the X-rays when the C-arm passes through a position located a predetermined distance before the predetermined position.

11. An apparatus according to claim 1, wherein the control unit generates a control signal for displaying predetermined image data when the C-arm reaches a predetermined position.

12. An apparatus according to claim 1, further comprising a present window generating unit which generates a preset window for presetting a movement pattern of the C-arm which corresponds to the input of the second user instruction.

13. An apparatus according to claim 1, which further comprises an image data storage unit which stores a plurality of image data, and a display unit which displays image data read out from the image data storage unit, and in which the control unit controls the image data storage unit to selectively read out specific image data, of said plurality of image data, which corresponds to a predetermined position when the C-arm reaches the predetermined position.

14. An apparatus according to claim 1, which further comprises an image data storage unit which stores a plurality of image data, and a display unit which displays image data read out from the image data storage unit, and in which the control unit controls the image data storage unit to selectively read out specific image data, of said plurality of image data, which corresponds to a position and direction of the C-arm.

* * * * *